US011160759B1

(12) United States Patent
Louw

(10) Patent No.: US 11,160,759 B1
(45) Date of Patent: *Nov. 2, 2021

(54) CAPSULE WITH INTERNAL DIAPHRAGM FOR IMPROVED BIOAVAILABILITY

(71) Applicant: ComboCap, Inc., New York, NY (US)

(72) Inventor: Tobias Johan Louw, New York, NY (US)

(73) Assignee: COMBOCAP, INC., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/767,010

(22) PCT Filed: Oct. 10, 2016

(86) PCT No.: PCT/US2016/056285
§ 371 (c)(1),
(2) Date: Apr. 9, 2018

(87) PCT Pub. No.: WO2017/062954
PCT Pub. Date: Apr. 13, 2017

Related U.S. Application Data

(60) Provisional application No. 62/239,435, filed on Oct. 9, 2015, provisional application No. 62/239,454, filed on Oct. 9, 2015, provisional application No. 62/239,442, filed on Oct. 9, 2015.

(51) Int. Cl.
A61K 9/48 (2006.01)
A61K 31/122 (2006.01)
A61K 31/201 (2006.01)
A61K 31/202 (2006.01)
A61K 31/01 (2006.01)
A61K 31/05 (2006.01)
A61K 31/203 (2006.01)
A61K 31/375 (2006.01)
A61K 31/525 (2006.01)
A61K 31/60 (2006.01)
A61K 33/06 (2006.01)
A61K 33/18 (2006.01)
A61K 33/26 (2006.01)
A61K 33/42 (2006.01)
A61K 47/12 (2006.01)
A61K 35/00 (2006.01)

(52) U.S. Cl.
CPC ............ *A61K 9/4808* (2013.01); *A61K 9/485* (2013.01); *A61K 9/4858* (2013.01); *A61K 9/4875* (2013.01); *A61K 31/01* (2013.01); *A61K 31/05* (2013.01); *A61K 31/122* (2013.01); *A61K 31/201* (2013.01); *A61K 31/202* (2013.01); *A61K 31/203* (2013.01); *A61K 31/375* (2013.01); *A61K 31/525* (2013.01); *A61K 31/60* (2013.01); *A61K 33/06* (2013.01); *A61K 33/18* (2013.01); *A61K 33/26* (2013.01); *A61K 33/42* (2013.01); *A61K 47/12* (2013.01); *A61K 2035/115* (2013.01)

(58) Field of Classification Search
None
See application file for complete search history.

(56) References Cited

U.S. PATENT DOCUMENTS

| 1,510,260 | A | | 9/1924 | Cyrenius | |
|---|---|---|---|---|---|
| 3,927,195 | A | * | 12/1975 | Messora | ................. A61J 3/071 424/454 |
| 4,339,428 | A | | 7/1982 | Tencza | |
| 5,223,265 | A | | 6/1993 | Wong | |
| 5,387,421 | A | | 2/1995 | Amidon et al. | |
| 5,394,980 | A | | 3/1995 | Tsai | |
| 7,670,612 | B2 | | 3/2010 | Miller | |
| 2003/0199481 | A1 | | 10/2003 | Garavani et al. | |
| 2005/0123603 | A1 | * | 6/2005 | Dalland | ................. A61K 31/12 424/456 |

(Continued)

FOREIGN PATENT DOCUMENTS

EP 2777802 A1 9/2014
NL 7610038 A 3/1978

(Continued)

OTHER PUBLICATIONS

Johnson www.merckmanuals.com/home/disorders-of-nutrition/vitamins/overview-of-vitamins# 9 pages (Year: 2020).*
Extended European Search Report for European Patent Application No. 16854535.8 dated Apr. 2, 2019.
Extended European Search Report for European Patent Application No. 16854536.6 dated Apr. 3, 2019.
Extended European Search Report for European Patent Application No. 16854537.4 dated Mar. 29, 2019.
International Search Report and Written Opinion for PCT/US2016/056276 dated Jan. 10, 2017.
International Search Report and Written Opinion for PCT/US2016/056285 dated Jan. 10, 2017.

(Continued)

Primary Examiner — Robert A Wax
Assistant Examiner — Caralynne E Helm
(74) Attorney, Agent, or Firm — Troutman Pepper Hamilton Sanders LLP

(57) ABSTRACT

A multi-compartment capsule may include a body, a diaphragm between, which seals off the body and provides a first compartment to hold an ingredient, and a cap applied to the body whereby a space between the inner portion of the cap and the diaphragm defines a second compartment for holding an oil. A two-compartment capsule may include a body, a diaphragm between, which seals off the body and provides a first compartment to hold an oil, and a cap applied to the body whereby a space between the inner portion of the cap and the diaphragm defines a second compartment for holding an ingredient. The ingredient may have increased bioavailability after exposure to the oil. This disclosure also provides particular formulations for use in such a capsule.

18 Claims, 6 Drawing Sheets

(56) References Cited

U.S. PATENT DOCUMENTS

| | | |
|---|---|---|
| 2006/0280794 A1 | 12/2006 | Hamaguchi et al. |
| 2007/0212411 A1 | 9/2007 | Fawzy et al. |
| 2007/0259034 A1* | 11/2007 | Steele .................. A61K 31/12 424/456 |
| 2008/0213320 A1 | 9/2008 | Eisenstein et al. |
| 2008/0287368 A1* | 11/2008 | Yu ...................... A61K 31/015 514/7.7 |
| 2009/0087483 A1 | 4/2009 | Sison |
| 2010/0048704 A1* | 2/2010 | Vermeer ............. A61K 31/122 514/560 |
| 2010/0209389 A1 | 8/2010 | McInnes et al. |
| 2012/0269868 A1* | 10/2012 | Faerstein ............ A61K 9/4825 424/400 |
| 2014/0212482 A1 | 7/2014 | Miller |
| 2014/0273150 A1 | 9/2014 | Angel |
| 2014/0302133 A1 | 10/2014 | Van Rooyen et al. |
| 2015/0246768 A1 | 9/2015 | Talon |
| 2016/0038425 A1* | 2/2016 | Fang ........................ A61J 3/07 424/451 |
| 2018/0289625 A1 | 10/2018 | Louw |
| 2018/0296489 A1 | 10/2018 | Louw |

FOREIGN PATENT DOCUMENTS

| | | |
|---|---|---|
| WO | 2013050973 A1 | 4/2013 |
| WO | 2014202412 A1 | 12/2014 |
| WO | 2017062951 A1 | 4/2017 |
| WO | 2017062956 A1 | 4/2017 |

OTHER PUBLICATIONS

International Search Report and Written Opinion for PCT/US2016/056293 dated Jan. 23, 2017.
Capsugele® capsule size reference 2 pages (Year: 2013).
Physical Properties of Fats and Oils reference www.dgfett.de/material/physikalische_eigenschaften.pdf 29 pages (Year: 2005).
Aspirin safety data sheet 7 pages (Year: 2015).
Cadé Vcaps® Plus Capsules 12 pages (Year: 2012).

* cited by examiner

CAPSULE WITH INTERNAL DIAPHRAGM FOR IMPROVED BIOAVAILABILITY

CROSS-REFERENCE TO RELATED APPLICATIONS

This application is a U.S. national stage filing under 35 U.S.C. § 371 of International Application No. PCT/US2016/056285 filed Oct. 10, 2016 entitled "Capsule with Internal Diaphragm for Improved Bioavailability," which claims priority to and benefit of U.S. Provisional Application No. 62/239,435 filed Oct. 9, 2015, entitled "Capsule with Volume-Adjustable Internal Diaphragm," U.S. Provisional Application No. 62/239,454 filed Oct. 9, 2015, entitled "Capsule with Internal Diaphragm for Improved Bioavailability," and U.S. Provisional Application No. 62/239,442 filed Oct. 9, 2015, entitled "Capsule with Internal Diaphragm and Solid Ingredients." The contents of each of these applications are hereby incorporated herein by reference in their entireties.

SUMMARY

Embodiments described herein are directed to a multi-compartment capsule comprising a body; a diaphragm, having two sidewalls and a bottom, extending into the body and defining a first compartment between an outer surface of the diaphragm and an inner surface of the body, adapted to hold an oil; and a cap mounted to an outer surface of the body and opposed to the diaphragm, and defining a second compartment between an inner surface of the diaphragm and the cap, adapted to hold an ingredient which has increased bioavailability after exposure to the oil; wherein the two sidewalls of the diaphragm extend along the inner surface of the body and are aligned with an open end of the body. In some embodiments, the capsule is a size 00 capsule. In some embodiments, the first compartment is hermetically sealed by the diaphragm.

In some embodiments, the oil is selected from the group consisting of omega-3 oil, red palm oil, fish oil, krill oil, walnut oil, saw palmetto oil, castor oil, garlic oil, flaxseed oil, canola oil, soybean oil, *Cannabis* oil, argan oil, coconut oil, peppermint oil, evening primrose oil, oregano oil, emu oil, cod liver oil, algae oil, grape seed oil, rose oil, clove oil, vitamin E oil, blueberry seed oil, raspberry seed oil, pumpkin seed oil, hemp oil, alpha-linolenic acid, and combinations thereof.

In some embodiments, the omega-3 oil is selected from the group consisting of alpha-linolenic acid, docosahexaenoic acid, eicosapentaenoic acid, krill oil, fish oil, walnut oil, flaxseed oil, canola oil, soybean oil, and combinations thereof.

In some embodiments, the ingredient is an oil, a liquid, a powder, a granule, a semi-solid, a gel, a beadlet, a microbead, a liquid, or a combination thereof.

In some embodiments, the ingredient is an oil, a probiotic, a botanical, an herbal extract, a digestive enzyme, a vitamin, a carotenoid, a collagen, a medicament, or a combination thereof.

In some embodiments, the bottom of the diaphragm may be flattened. In some embodiments, the bottom of the diaphragm may be curved. In some embodiments, the bottom of the diaphragm may be substantially or partially flattened.

In some embodiments, the oil comprises an omega-3 oil and the ingredient is a multivitamin powder, or a multivitamin powder and coenzyme Q10.

In some embodiments, the oil comprises an omega-3 oil and the ingredient is a statin, or a statin and coenzyme Q10.

In some embodiments, the oil comprises an omega-3 oil and the ingredient is vitamin K2.

In some embodiments, the oil comprises alpha-linolenic acid and the ingredient is selected from chromium, or chromium and coenzyme Q10.

In some embodiments, the oil is saw palmetto oil and the ingredient is a liothyronine sodium (T3) powder.

In some embodiments, the oil is red palm oil, and the ingredient is selected from vitamin D, vitamin K2, a multivitamin or a combination thereof.

In some embodiments, the oil is an omega-3 oil, and the ingredient is selected from aspirin, a statin, or a combination thereof.

Some embodiments described herein are directed to a multi-compartment capsule comprising a body; a diaphragm, having two sidewalls and a bottom, extending into the body and defining a first compartment between an outer surface of the diaphragm and an inner surface of the body, adapted to hold an ingredient; and a cap mounted to an outer surface of the body and opposed to the diaphragm, and defining a second compartment between an inner surface of the diaphragm and the cap, adapted to hold an oil; wherein the two sidewalls of the diaphragm extend along the inner surface of the body and are aligned with an open end of the body.

In some embodiments, the second compartment is sealed to prevent oil leakage.

In some embodiments, the ingredient has increased bioavailability upon exposure to the oil.

DETAILED DESCRIPTION

Figure 1:
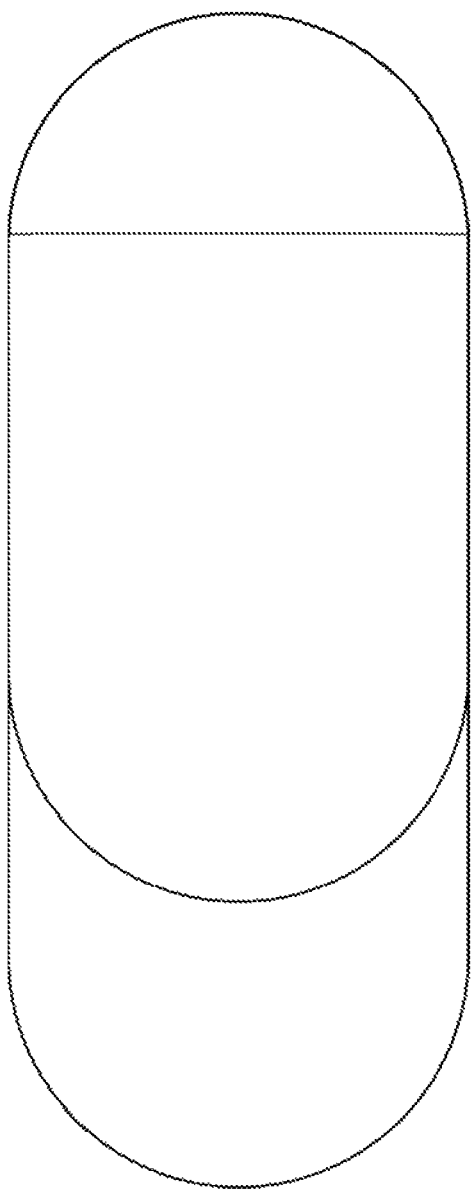
FIG. 1 illustrates a cross-sectional view of a capsule of embodiments herein wherein the first (lower) compartment has a volume of about 423 mm$^3$ and the second (upper) compartment has a volume of about 497 mm$^3$, and wherein the first compartment comprises an oil and the second compartment comprises an ingredient.
Figure 2:
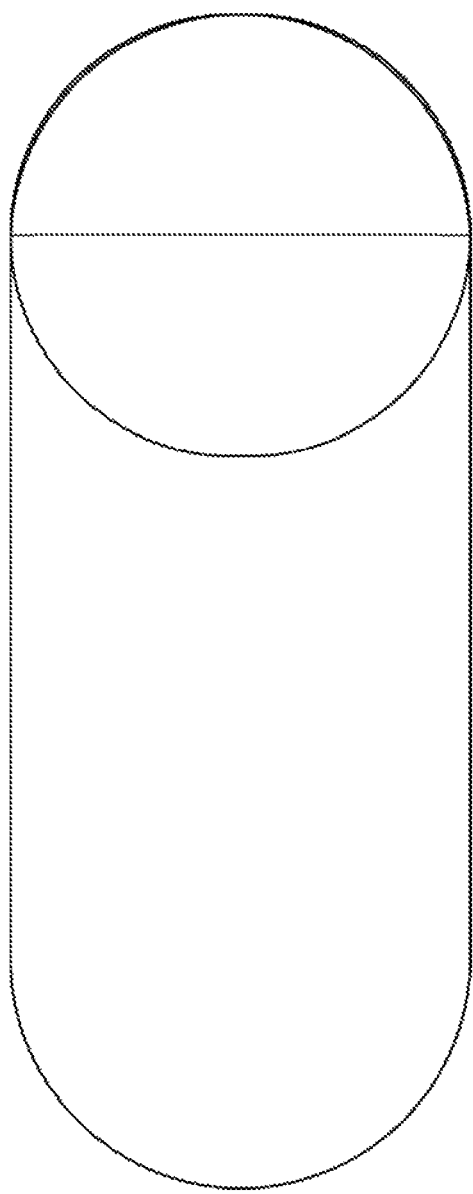
FIG. 2 illustrates a cross-sectional view of a capsule of embodiments herein wherein the first (lower) compartment has a volume of 743 mm$^3$ and the second (upper) compartment has a volume of 176 mm$^3$, and wherein the first compartment comprises an oil and the second compartment comprises an ingredient.
Figure 3:
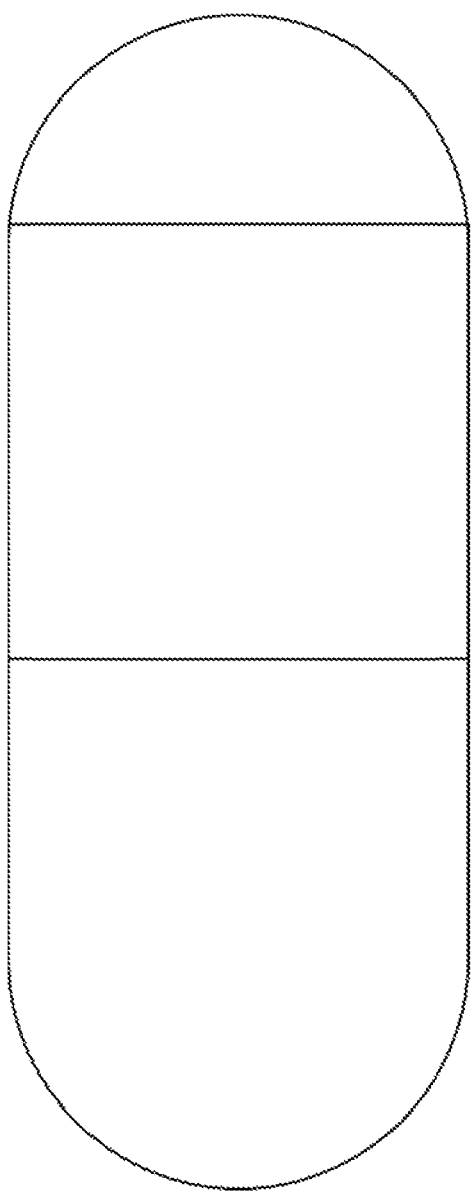
FIG. 3 illustrates a cross-sectional view of a capsule of embodiments herein with a flattened bottom, wherein each compartment comprises a solid ingredient.
Figure 4A:
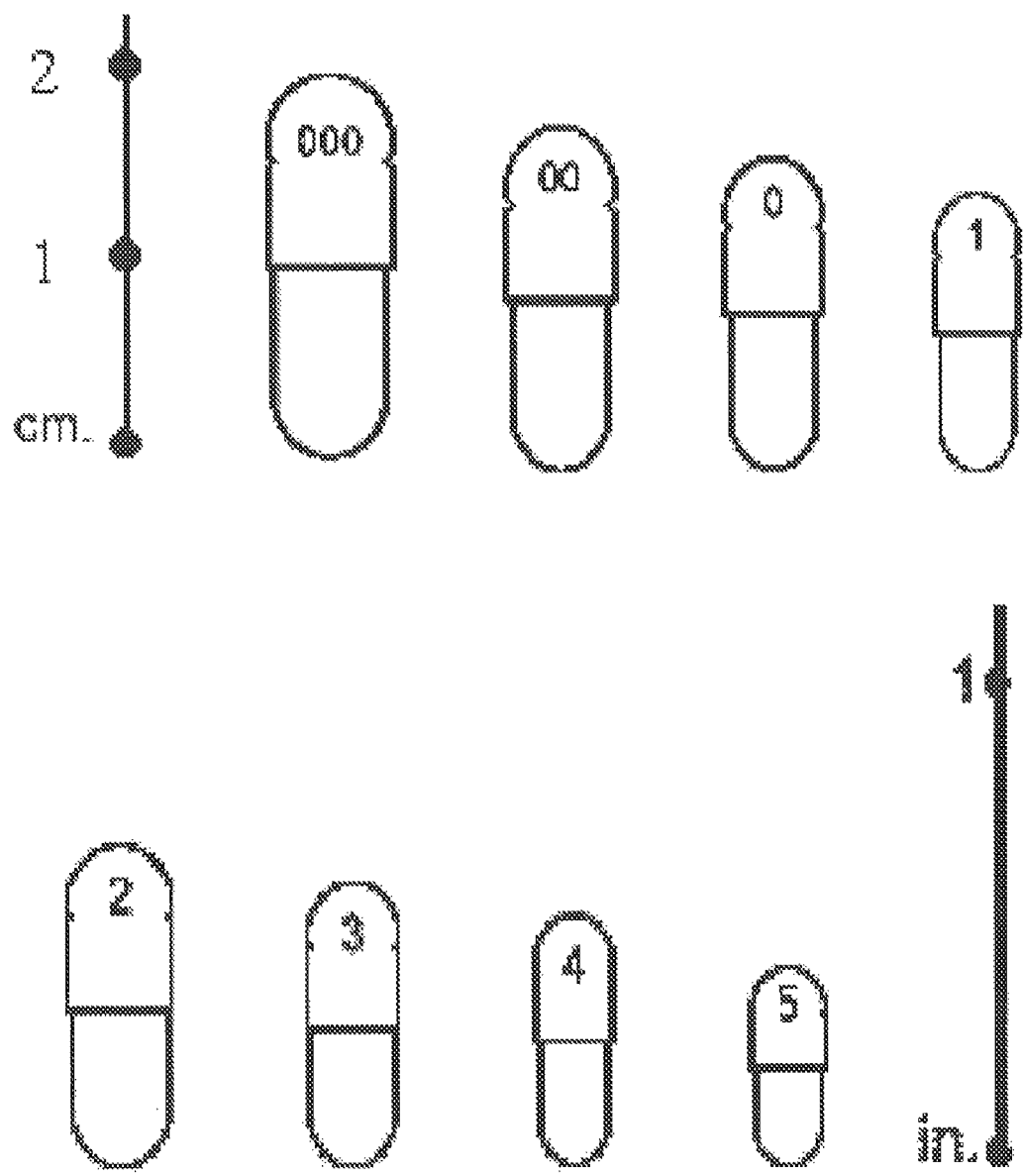
FIGS. 4A, 4B, and 4C illustrate standard and elongated TORPAC capsule sizes, which may be used in some embodiments described herein.
Figure 4B:
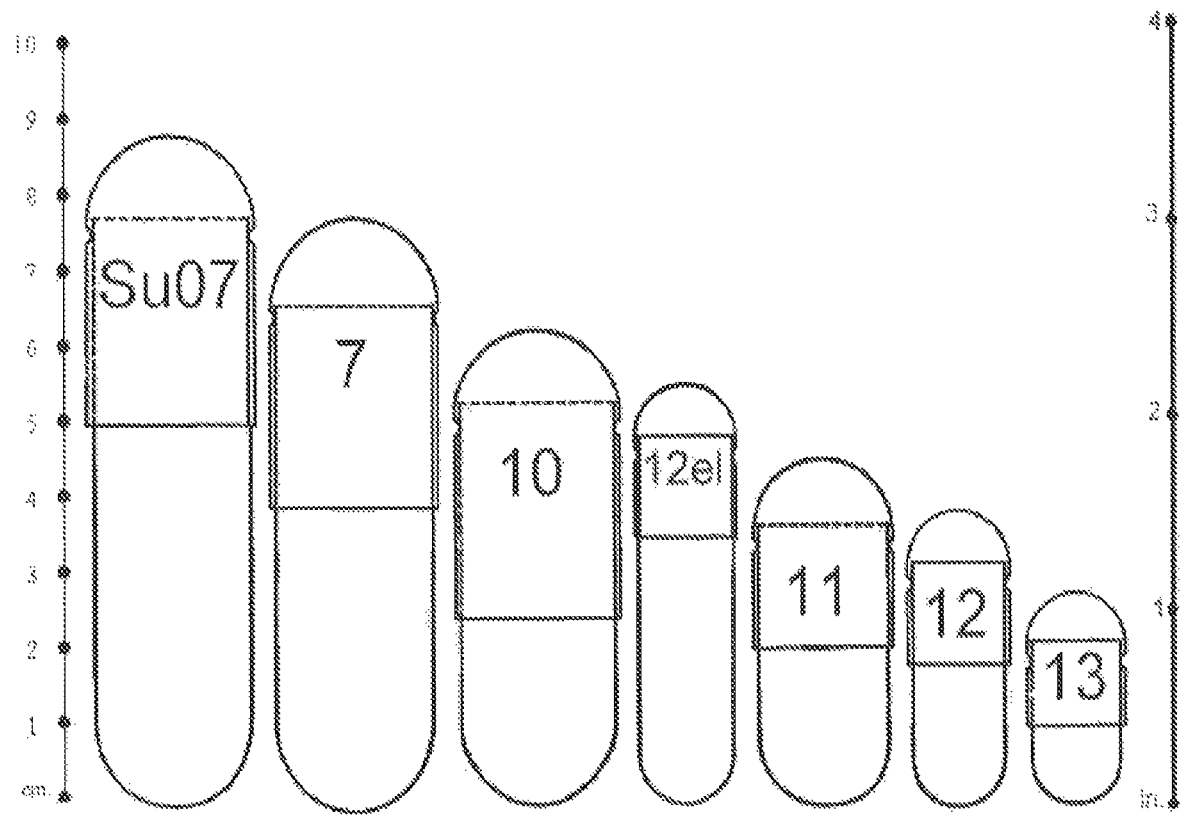
Figure 4C:
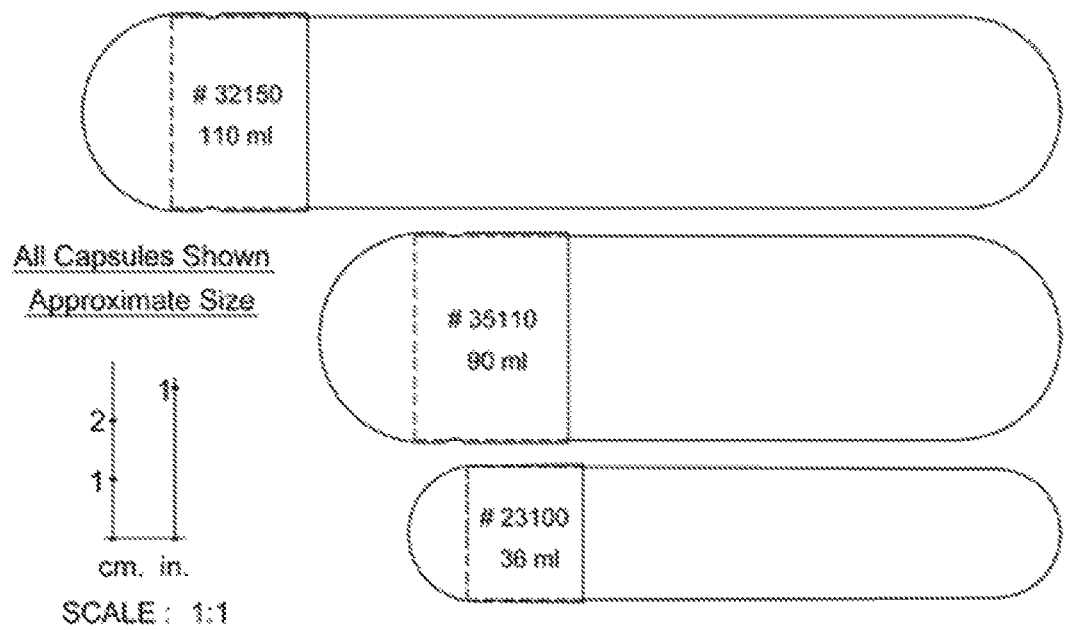

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention, which will be limited only by the appended claims. Unless defined otherwise, all technical and scientific terms used herein have the same meanings as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entireties. Nothing herein is to be construed as an admission that the invention is not entitled to antedate such disclosure by virtue of prior invention.

It must also be noted that as used herein and in the appended claims, the singular forms "a," "an," and "the" include plural references unless the context clearly dictates otherwise. Thus, for example, reference to "an ingredient" is a reference to one or more ingredients and equivalents thereof known to those skilled in the art, and so forth.

As used herein, the term "about" means plus or minus 10% of the numerical value of the number with which it is being used. Therefore, about 50 mg means in the range of 45 mg-55 mg.

The term "patient" or "subject" as used herein is an animal, particularly a human, suffering from an unwanted disease or condition that may be treated by the therapeutics and/or compositions described herein.

"Optional" or "optionally" means that the subsequently described event or circumstance may or may not occur, and that the description includes instances where the event occurs and instances where it does not.

Throughout the specification of the application, various terms are used such as "primary," "secondary," "first," "second," and the like. These terms are words of convenience used to distinguish between different elements, and such terms are not intended to limit how the different elements may be used.

As used herein, the term "medicament" or "therapeutic" means an agent used to treat, combat, ameliorate, prevent or improve an unwanted condition or disease of a subject.

A "therapeutically effective amount" or "effective amount" of a composition is an amount necessary or sufficient to achieve the desired result. The activity contemplated by the embodiments herein includes medically therapeutic, cosmetically therapeutic and/or prophylactic treatment, as appropriate. A therapeutically effective amount of the compound of embodiments herein is typically an amount such that when it is administered in a physiologically tolerable excipient composition, it is sufficient to achieve an effective systemic concentration or local concentration in or on the tissue to achieve the desired therapeutic or clinical outcome.

The terms "treat," "treated," or "treating," as used herein, refer to therapeutic treatment, cosmetic treatment, and/or prophylactic or preventative measures, wherein the object is to prevent or slow down (lessen) an undesired physiological condition, disorder, or disease, or to obtain beneficial or desired clinical results. For the purposes of this invention, beneficial or desired clinical results include, but are not limited to, alleviation of symptoms; diminishment of the extent of the condition, disorder, or disease; stabilization (i.e., not worsening) of the state of the condition, disorder, or disease; delay in onset or slowing of the progression of the condition, disorder, or disease; amelioration of the condition, disorder, or disease state; and remission (whether partial or total), whether detectable or undetectable, or enhancement or improvement of the condition, disorder, or disease. Treatment includes eliciting a clinically significant response without excessive levels of side effects.

As used herein, the term "consists of" or "consisting of" means that the formulation includes only the elements, steps, or ingredients specifically recited in the particular claimed embodiment or claim.

As used herein, the term "consisting essentially of" or "consists essentially of" means that the only active pharmaceutical ingredient in the formulation or method that treats the specified condition is the specifically recited therapeutic in the particular embodiment or claim.

Capsules are typically manufactured in certain standard sizes, such as TORPAC sizes, referred to as a capsule size designated by numerals, such as 000, 00, etc. Such capsules typically have two parts: a cap and a body, which are bonded or fitted together. One of the most common sizes is the 00 capsule. The typical size 00 capsule, in common with other capsules, has a standardized nominal volume. For instance, a size 00 capsule has a volume of approximately 0.95 milliliters. In some embodiments described below, the multi-compartment capsule is a size 00 capsule. In some embodiments, the capsule size may be size 000, size 0, size 1, size 2, size 3, size 4, or size 5, or any non-standard size in between these sizes. In some embodiments described below, the capsule size may be elongated ("EL"), such that the size may be, for example, 00 EL. In some embodiments, the elongation may be to any standard length or to a non-standard length. In some embodiments, the elongated capsule may add from about 50 mm$^3$ to about 150 mm$^3$ of additional volume to the first compartment, the second compartment, or a combination thereof. In some embodiments, the elongated capsule may add about 110 mm$^3$ of additional volume to the first compartment, the second compartment, or a combination thereof. In some embodiments, if the diaphragm's diameter is reduced, it may be possible to insert a longer diaphragm into the capsule, thereby changing the available volumes in both the first and second compartments. In some embodiments, scaling the dimensions of the multi-compartment capsule described herein may result in a larger or smaller capsule with substantially the same ratios as described herein. In some embodiments, scaling the dimensions of the multi-compartment capsule described herein may result in a larger or smaller capsule with ratios different from those described herein.

Exemplary benefits of such two-compartment capsules may include increased patient compliance, a double-chamber controlled release, increased efficacy or bioavailability of ingredients due to co-administration, increased stability, and the ability to formulate difficult combinations of ingredients into one capsule, such as incompatible actives which can now be co-administered.

For some applications, it may be advantageous to deliver one or more ingredients in the form of a capsule with two compartments. For some applications, it may advantageous for the one or more ingredients delivered in such a capsule to be ingredients which have improved bioavailability when dissolved in one or more oils.

Embodiments described herein are directed to a multi-compartment capsule comprising a body; a diaphragm, having two sidewalls and a bottom, extending into the body and defining a first compartment between an outer surface of the diaphragm and an inner surface of the body; and a cap mounted to an outer surface of the body and opposed to the diaphragm, and defining a second compartment between an inner surface of the diaphragm and the cap; wherein the two sidewalls of the diaphragm extend along the inner surface of the body and are aligned with an open end of the body. In some embodiments, the capsule is a size 00 capsule.

In some embodiments, the multi-compartment capsule may comprise a body; a diaphragm, having two sidewalls and a bottom, extending into the body and forming a first compartment defined by a first surface of the diaphragm and the body; and a cap mounted to the body and opposed to the diaphragm, the cap forming a second compartment defined by an opposing surface of the diaphragm and the cap; wherein the two sidewalls of the diaphragm extend along the inner surface of the body and are aligned with an open end of the body; and wherein the first compartment and the second compartment are each adapted to hold one or more solid ingredients. In some embodiments, the first compartment is hermetically sealed by the diaphragm. In some embodiments, the one or more solid ingredients comprises an oil, a liquid, a powder, a granule, a semi-solid, a microbead, a beadlet, or a combination thereof.

In some embodiments, the bottom of the diaphragm may be flattened. A flatter bottom may allow for more volume in the lower compartment. In some embodiments, the bottom of the diaphragm may be curved. In some embodiments, the bottom of the diaphragm may be substantially or partially flattened.

In some embodiments, the contents of the first compartment and the contents of the second compartment may be released simultaneously. This simultaneous release may occur because each end of the multi-compartment capsule comprises the same or substantially the same material composition and thickness, such that when the capsule is digested, both compartments are degraded simultaneously. This simultaneous release may be advantageous in some embodiments wherein the contents of the first compartment and the contents of the second compartment may provide improved bioavailability or other synergistic effects when combined by such a release.

In some embodiments, the first compartment comprises an oil. In some embodiments, the second compartment comprises an ingredient. In some embodiments, the second ingredient is adapted to hold an ingredient which has increased bioavailability after exposure to the oil. In some embodiments, the first compartment comprises an ingredient having increased bioavailability after exposure to oil and the second compartment comprises an oil. Exemplary formulations described below could be used with oil in either compartment.

In some embodiments, the two sidewalls of the diaphragm extend along the inner surface of the body and are aligned with an open end of the body. In some embodiments, the capsule is a size 00 capsule. In some embodiments, the first compartment is hermetically sealed by the insertion and sealing of the diaphragm into the capsule body.

In some embodiments, the bottom of the diaphragm may be flattened. In some embodiments, the bottom of the diaphragm may be curved. In some embodiments, the bottom of the diaphragm may be substantially or partially flattened.

In some embodiments, the oil is selected from the group consisting of omega-3 oil, red palm oil, fish oil, krill oil, walnut oil, saw palmetto oil, castor oil, garlic oil, flaxseed oil, canola oil, soybean oil, *Cannabis* oil, argan oil, coconut oil, peppermint oil, evening primrose oil, oregano oil, emu oil, cod liver oil, algae oil, grape seed oil, rose oil, clove oil, vitamin E oil, blueberry seed oil, raspberry seed oil, pumpkin seed oil, hemp oil, alpha-linolenic acid, conjugated linoleic acid, docosahexaenoic acid, ginger oil, lavender oil, and combinations thereof.

In some embodiments, the omega-3 oil is selected from the group consisting of alpha-linolenic acid, docosahexaenoic acid, eicosapentaenoic acid, krill oil, fish oil, walnut oil, flaxseed oil, canola oil, soybean oil, and combinations thereof. The omega-3 oil may be in an amount of about 10 mg to about 2000 mg.

In some embodiments, the oil may comprise a form or derivative of vitamin E In some embodiments, the oil may comprise from about 10 mg to about 500 mg of a form or derivative of vitamin E In some embodiments, the form or derivative of vitamin E may be a tocotrienol, such as, for example, alpha tocotrienol, beta tocotrienol, gamma tocotrienol, delta tocotrienol, or any combination thereof.

In some embodiments, the ingredient is an oil, a liquid, a powder, a granule, a semi-solid, a gel, a beadlet, a microbead, a liquid, or a combination thereof. In some embodiments, the ingredient is an oil, a probiotic, a botanical, an herbal extract, a digestive enzyme, a vitamin, a carotenoid, a collagen, a medicament, or a combination thereof. In some embodiments, the ingredient may comprise alpha-carotene, beta-carotene, biotin, cadmium, caffeine, calcium, cinnamon, copper, curcumin, dexmethylphenidate, dicalcium phosphate, docosahexaenoic acid, folic acid, frankincense, glucosamine, gymnema, gymnema extract, iodine, iron, linoleic acid, lipoic acid, LOWAT, lutein, lycopene, magnesium, magnesium stearate, manganese, melatonin, molybdenum, niacin, oleic acid, palmitic, panthothenic acid, passion flower, phosphorus, a plant sterol, resvida, selenium, squalene, *Ginseng*, tocopherols, vitamin A, vitamin B1, vitamin B2, vitamin B6, vitamin C, vitamin K, zinc, or a combination thereof.

In some embodiments, the ingredient comprises a pharmaceutical agent. In some embodiments, the pharmaceutical agent is selected from the group consisting of aspirin, a statin, ipriflavone, cohosh, castus, coenzyme Q10 (CoQ10), gauifenesin, althea root, antimony pentasulfide, creosote, guaiacolsulfonate, ipecacuanha (syrup of ipecac), levoverbenone, potassium iodide, senega, tyloxapol, ammonium chloride, salbutamol, albuterol, levosalbutamol, levalbuterol, pirbuterol, epinephrine, ephedrine, terbutaline, salmeterol, clenbuterol, formoterol, bambuerol, indacaterol, ephrinesulfate, ticlopidine, clopidogrel, prasugrel, ticagrelor, cilostazol, vorapaxar, trifusal, dipyridamole, a tocotrienol, triiodothyronine (T3), liothyronine sodium, and combinations thereof.

In some embodiments, the ingredient comprises aspirin. In some embodiments, the aspirin comprises from about 10 mg to about 500 mg. In some embodiments, the aspirin comprises from about 81 mg to about 324 mg. In some embodiments, one of the first or second compartment comprises aspirin in an amount of about 10 mg to about 500 mg.

In some embodiments, the ingredient comprises a statin. The statin may be selected from the group consisting of atorvastatin, fluvastatin, lovastatin, pitavastatin, pravastatin, rosuvastatin, simvastatin, and combinations thereof. The statin may be in an amount of about 1 mg to about 100 mg. In some embodiments, the statin may be in an amount of about 5 mg to about 40 mg. In some embodiments, one of the first or second compartment comprises a statin in an amount of about 1 mg to about 100 mg.

In some embodiments, the first compartment comprises aspirin in an amount of about 10 mg to about 500 mg and the second compartment comprises an oil in an amount of about 10 mg to about 2000 mg. In some embodiments, the oil is an omega-3 oil.

In some embodiments, the capsule may include omega-3 oil with or without red palm oil in the first compartment, and CoQ10 in the second compartment. The omega-3 oil may be in an amount of about 10 mg to about 2000 mg. The red palm oil may be in an amount of about 10 mg to about 2000 mg. The CoQ10 may be in an amount of about 10 mg to about 1000 mg.

In some embodiments, the oil comprises an omega-3 oil and the ingredient is a multivitamin, or a multivitamin and coenzyme Q10. The omega-3 oil may be in an amount of about 10 mg to about 2000 mg. The CoQ10 may be in an amount of about 10 mg to about 1000 mg. The multivitamin may be in an amount of about 1 mg to about 5000 mg.

In some embodiments, the oil comprises an omega-3 oil and the ingredient is a statin, or a statin and coenzyme Q10. The omega-3 oil may be in an amount of about 10 mg to about 2000 mg. The statin in an amount of about 1 mg to about 100 mg. The CoQ10 may be in an amount of about 10 mg to about 1000 mg.

In some embodiments, the oil comprises an omega-3 oil and the ingredient is vitamin K2. The omega-3 oil may be in an amount of about 10 mg to about 2000 mg. The vitamin K2 may be in an amount of about 10 mcg to about 1000 mcg.

In some embodiments, the oil comprises alpha-linolenic acid and the ingredient is selected from chromium, or chromium and coenzyme Q10. The alpha linolenic acid may be in an amount of about 10 mg to about 500 mg. The chromium may be in an amount of about 10 mcg to about 1000 mcg. The CoQ10 may be in an amount of about 10 mg to about 1000 mg.

In some embodiments, the oil is saw palmetto oil and the ingredient is liothyronine sodium (T3). The saw palmetto oil may be in an amount of about 10 mg to about 1000 mg. The liothyronine sodium may be in an amount of about 5 mcg to about 500 mcg.

In some embodiments, the oil is red palm oil, and the ingredient is selected from vitamin D, vitamin K2, a multivitamin or a combination thereof. The red palm oil may be in an amount of about 10 mg to about 2000 mg. The vitamin D may be in an amount of about 10 IU to about 3000 IU. The vitamin K2 may be in an amount of about 10 mcg to about 1000 mcg. The multivitamin may be in an amount of about 1 mg to about 5000 mg.

In some embodiments, the oil is red palm oil, and the ingredient is selected from lutein, lycopene, biotin, selenium, selenium (methionine), zinc, zinc (glyconate), or a combination thereof. The red palm oil may be in an amount of about 10 mg to about 2000 mg. The lutein may be in an amount of about 1 mg to about 30 mg. The lycopene may be in an amount of about 1 mg to about 30 mg. The biotin may be in an amount of about 0.01 mg to about 10 mg. The selenium or selenium (methionine) may be in an amount of about 1 mcg to about 200 mcg. The zinc or zinc (glyconate) may be in an amount of about 1 mg to about 45 mg.

In some embodiments, the oil is an omega-3 oil and the ingredient is selected from frankincense, gymnema, gymnema extract, cinnamon, chromium, chromium (picolinate), vitamin B6, vitamin B12, or a combination thereof. The omega-3 oil may be in an amount of about 10 mg to about 2000 mg. The frankincense may be in an amount of about 1 mg to about 500 mg. The gymnema or gymnema extract may be in an amount of about 10 mg to about 1000 mg. The cinnamon may be in an amount of about 10 mg to about 1000 mg. The chromium or chromium (picolinate) may be in an amount of about 10 mg to about 1000 mg. The vitamin B6 may be in an amount of about 10 mg to about 1000 mg. The vitamin B12 may be in an amount of about 10 mcg to about 1000 mcg.

In some embodiments, the oil is an omega-3 oil, and the ingredient is selected from resvida, lipoic acid, CoQ10, folic acid, vitamin B6, vitamin B12, or a combination thereof. The omega-3 oil may be in an amount of about 10 mg to about 2000 mg. The resvida may be in an amount of about 10 mg to about 1000 mg. The amount of lipoic acid may be in an amount of about 1 mg to about 1000 mg. The CoQ10 may be in an amount of about 10 mg to about 1000 mg. The folic acid may be in an amount of about 0.1 mcg to about 1000 mcg. The vitamin B6 may be in an amount of about 10 mg to about 1000 mg. The vitamin B12 may be in an amount of about 10 mcg to about 1000 mcg.

In some embodiments, the oil is selected from krill oil, red palm oil, or a combination thereof, and the ingredient is selected from oleic acid, linoleic acid, tocotrienols, tocopherols, beta-carotene, alpha-carotene, squalene, a plant sterol, CoQ10, a multivitamin, or a combination thereof. The krill oil may be in an amount of about 10 mg to about 2000 mg. The red palm oil may be in an amount of about 10 mg to about 2000 mg. The oleic acid may be in an amount of about 10 mg to about 1000 mg. The linoleic acid may be in an amount of about 1 mg to about 1000 mg. The tocotrienols may be in an amount of about 1 mg to about 1000 mg. The tocopherols may be in an amount of about 1 mg to about 1000 mg. The beta-carotene may be in an amount of about 1 mg to about 1000 mg. The alpha-carotene may be in an amount of about 1 mg to about 1000 mg. The squalene may be in an amount of about 0.1 mg to about 1000 mg. The plant sterol may be in an amount of about 1 mg to about 1000 mg. The CoQ10 may be in an amount of about 0.01 mg to about 1000 mg. The multivitamin may be in an amount of about 1 mg to about 5000 mg.

In some embodiments, the oil is selected from krill oil, an omega-3 oil such as, for example, docosahexaenoic acid (DHA), or a combination thereof, and the ingredient is selected from vitamin C, zinc, dicalcium phosphate, vitamin D, vitamin K, magnesium, calcium, or a combination thereof. The krill oil may be in an amount of about 10 mg to about 2000 mg. The DHA may be in an amount of about 10 mg to about 2000 mg. The vitamin C may be in an amount of about 1 mg to about 1000 mg. The zinc may be in an amount of about 1 mg to about 1000 mg. The dicalcium phosphate may be in an amount of about 1 mg to about 1000 mg. The vitamin D may be in an amount of about 10 IU to about 3000 IU. The vitamin K may be in an amount of about 10 mcg to about 1000 mcg. The magnesium may be in an amount of about 0.1 mg to about 1000 mg. The calcium may be in an amount of about 1 mg to about 1000 mg.

In some embodiments, the oil is krill oil, and the ingredient is selected from a multivitamin, CoQ10, vitamin A, vitamin D, vitamin D3, vitamin E, biotin, folic acid, niacin, panthothenic acid, vitamin B1, vitamin B2, vitamin B6, vitamin B12, vitamin C, vitamin K, calcium, chromium, copper, iodine, magnesium, magnesium stearate, manganese, molybdenum, phosphorus, selenium, zinc, or a combination thereof. The krill oil may be in an amount of about 10 mg to about 2000 mg. The multivitamin may be in an amount of about 1 mg to about 5000 mg. The CoQ10 may be in an amount of about 0.01 mg to about 1000 mg. The vitamin A may be in an amount of about 10 IU to about 4000 IU. The vitamin D or vitamin D3 may be in an amount of about 10 IU to about 3000 IU. The vitamin E may be in amount of about 10 IU to about 3000 IU. The biotin may be in an amount of about 10 mcg to about 1000 mcg. The folic acid may be in an amount of about 0.1 mcg to about 1000 mcg. The niacin may be in an amount of about 1 mg to about 1000 mg. The panthothenic acid may be in an amount of about 1 mg to about 1000 mg. The vitamin B1 may be in an amount of about 1 mg to about 1000 mg. The vitamin B2 may be in an amount of about 1 mg to about 1000 mg. The vitamin B2 may be in an amount of about 1 mg to about 1000 mg. The vitamin B6 may be in an amount of about 1 mg to about 1000 mg. The vitamin B12 may be in an amount of about 10 mcg to about 1000 mcg. The vitamin C may be in an amount of about 1 mg to about 1000 mg. The vitamin K may be in an amount of about 10 mcg to about 1000 mcg. The calcium may be in an amount of about 1 mg to about 1000 mg. The chromium may be in an amount of about 1 mcg to about 1000 mcg. The copper may be in an amount of about 0.1 mg to about 100 mg. The iodine may be in an amount of about 0.01 mg to about 100 mg. The magnesium may be in an amount of about 0.1 mg to about 1000 mg. The magnesium stearate may be in an amount of about 0.1 mg to about 1000 mg. The manganese may be in an amount of about 0.1 mg to about 100 mg. The molybdenum may be in an amount of about 1 mcg to about 1000 mcg. The phosphorous may be in an amount of about 1 mg to about 100 mg. The selenium may be in an amount of about 1 mcg to about 200 mcg. The zinc may be in an amount of about 1 mg to about 1000 mg.

In some embodiments, the oil is red palm oil, and the ingredient is selected from *Ginseng*, CoQ10, vitamin B12, caffeine, caffeine beadlets, or a combination thereof. The red palm oil may be in an amount of about 10 mg to about 2000 mg. The *Ginseng* may be in an amount of about 10 mg to about 1000 mg. The CoQ10 may be in an amount of about 0.01 mg to about 1000 mg. The vitamin B12 may be in an amount of about 10 mcg to about 1000 mcg. The caffeine or caffeine beadlets may be in an amount of about 1 mg to about 1000 mg.

In some embodiments, the oil is krill oil, and the ingredient is selected from vitamin D, vitamin D3, calcium, or a combination thereof. The krill oil may be in an amount of about 10 mg to about 2000 mg. The vitamin D or vitamin D3 may be in an amount of about 10 IU to about 3000 IU. The calcium may be in an amount of about 1 mg to about 1000 mg.

In some embodiments, the oil is an omega-3 oil, and the ingredient is a probiotic. The omega-3 oil may be in an amount of about 10 mg to about 2000 mg. The probiotic may be in an amount of about 1 million to about 100 million CFUs.

In some embodiments, the oil is krill oil, and the ingredient is selected from vitamin K2, glucosamine, collagen, UC2 collagen, or a combination thereof. The krill oil may be in an amount of about 10 mg to about 2000 mg. The vitamin K2 may be in an amount of about 0.01 mg to about 100 mg. The glucosamine may be in an amount of about 10 mg to about 1000 mg. The collagen or UC2 collagen may be in amount of about 1 mg to about 1000 mg.

In some embodiments, the oil is an omega-3 oil such as, for example, alpha-linolenic acid (ALA), and the ingredient is selected from caffeine, caffeine beadlets, or a combination thereof. The ALA may be in an amount of about 10 mg to about 2000 mg. The caffeine or caffeine beadlets may be in an amount of about 1 mg to about 1000 mg.

In some embodiments, the oil is ginger oil and the ingredient is curcumin. The ginger oil may be in an amount of about 10 mg to about 2000 mg, and the curcumin may be in an amount of about 10 mg to about 1000 mg.

In some embodiments, the oil is an omega-3 oil, and the ingredient is selected from vitamin D, vitamin D3, vitamin E, folic acid, vitamin B2, vitamin B6, vitamin B12, vitamin C, iron, dicalcium phosphate, or a combination thereof. The omega-3 oil may be in an amount of about 10 mg to about 2000 mg. The vitamin D or vitamin D3 may be in an amount of about 10 IU to about 3000 IU. The vitamin E may be in an amount of about 1 IU to about 3000 IU. The folic acid may be in an amount of about 0.1 mcg to about 1000 mcg. The vitamin B2 may be in an amount of about 1 mg to about 1000 mg. The vitamin B6 may be in an amount of about 1 mg to about 1000 mg. The vitamin B12 may be in an amount of about 1 mcg to about 1000 mcg. The vitamin C may be in an amount of about 1 mg to about 1000 mg. The iron may be in an amount of about 1 mg to about 1000 mg. The dicalcium phosphate may be in an amount of about 1 mg to about 1000 mg.

In some embodiments, the oil is krill oil and the ingredient is selected from vitamin D, vitamin D3, vitamin K2, vitamin E, vitamin E tocotrienols, or a combination thereof. The krill oil may be in an amount of about 10 mg to about 2000 mg. The vitamin D or vitamin D3 may be in an amount of about 10 IU to about 3000 IU. The vitamin K2 may be in an amount of about 0.01 mg to about 100 mg. The vitamin E or vitamin E tocotrienols may be in an amount of about 10 mg to about 1000 mg.

In some embodiments, the oil is lavender oil, and the ingredient is selected from melatonin, passion flower, lemon, lemon extract, or a combination thereof. The lavender oil may be in an amount of about 10 mg to about 2000 mg. The melatonin may be in an amount of about 1 mg to about 1000 mg. The passion flower may be in an amount of about 10 mg to about 1000 mg. The lemon or lemon extract may be in an amount of about 10 mg to about 1000 mg.

In some embodiments, the oil is conjugated linoleic acid (CLA), and the ingredient is selected from piper betle leaf, *Dolichos* bilforus seed extract, or a combination thereof, such as LOWAT. The CLA may be in an amount of about 10 mg to about 2000 mg. The piper betle leaf, *Dolichos* bilforus seed extract, or combination thereof, such as LOWAT, may be in an amount of about 10 mg to about 1000 mg.

In some embodiments, the oil is krill oil, and the ingredient is aspirin. The krill oil may be in an amount of about 10 mg to about 2000 mg, and the aspirin may be in an amount of about 10 mg to about 500 mg.

In some embodiments, the first compartment and the second compartment each has sufficient volume to administer a therapeutically effective dose of the oil and the ingredient, respectively.

Table 1 below lists some possible combinations of ingredients which may be found in some embodiments. It is to be understood that any of the ingredients within Table 1 may be found in any combination, and may be found in either compartment of the capsule described herein. It is to be further understood that the embodiments described in Table 1 are not meant to be limiting, but are merely illustrative.

TABLE 1

| First compartment | Second compartment |
| --- | --- |
| About 10 mg to about 500 mg of aspirin | About 10 mg to about 2000 mg of an oil |
| About 10 mg to about 500 mg of aspirin | About 10 mg to about 2000 mg of an omega-3 oil |

TABLE 1-continued

| First compartment | Second compartment |
|---|---|
| About 10 mg to about 2000 mg of an omega-3 oil; and/or | About 10 mg to about 1000 mg of CoQ10 |
| About 10 mg to about 2000 mg of red palm oil | |
| About 10 mg to about 2000 mg of an omega-3 | About 1 mg to about 100 mg of a statin; oil and/or |
| | About 10 mg to about 1000 mg of CoQ10 |
| About 10 mg to about 2000 mg of an omega-3 oil | About 10 mcg to about 1000 mcg of vitamin K2 |
| About 10 mg to about 500 mg of alpha linolenic acid | About 10 mcg to about 1000 mcg of chromium; and/or |
| | About 10 mg to about 1000 mg of CoQ10 |
| About 10 mg to about 1000 mg of saw palmetto oil | About 5 mcg to about 500 mcg of liothyronine sodium |
| About 10 mg to about 2000 mg of red palm oil | About 10 IU to about 3000 IU of vitamin D; and/or |
| | About 10 mcg to about 1000 mcg of vitamin K2; and/or |
| | About 1 mg to about 5000 mg of a multivitamin |
| About 10 mg to about 2000 mg krill oil | About 10 mg to about 1000 mg of CoQ10; and/or |
| | About 1 mg to about 5000 mg of a multivitamin |
| About 5 mcg to about 500 mcg of triiodothyronine | About 10 mg to about 1000 mg of vitamin B6; and/or |
| | About 10 mcg to about 1000 mcg of vitamin B12 |
| About 10 mg to about 2000 mg of krill oil | About 10 mcg to about 1000 mcg of vitamin K2 |
| About 10 mg to about 1000 mg of saw palmetto oil | About 5 mcg to about 500 mcg of triiodothyronine |
| About 10 mg to about 2000 mg of red palm oil | About 1 mg to about 30 mg of lutein; and/or |
| | About 1 mg to about 30 mg of lycopene; and/or |
| | About 0.01 mg to about 10 mg of biotin; and/or |
| | About 1 mcg to about 200 mcg of selenium (methionine); and/or |
| | About 1 mg to about 45 mg of zinc (glyconate) |
| About 10 mg to about 2000 mg of an omega-3 oil | About 1 mg to about 500 mg of frankincense; and/or |
| | About 10 mg to about 1000 mg of gymnema or gymnema extract; and/or |
| | About 10 mg to about 1000 mg of cinnamon; and/or |
| | About 10 mg to about 1000 mg of chromium (picolinate); and/or |
| | About 10 mg to about 1000 mg of vitamin B6; and/or |
| | About 10 mcg to about 1000 mcg of vitamin B12 |
| About 10 mg to about 2000 mg of an omega-3 oil | About 10 mg to about 1000 mg of resvida; and/or |
| | About 1 mg to about 1000 mg of lipoic acid; and/or |
| | About 10 mg to about 1000 mg of CoQ10; and/or |
| | About 0.1 mcg to about 1000 mcg of folic acid; and/or |
| | About 10 mg to about 1000 mg of vitamin B6; and/or |
| | About 10 mcg to about 1000 mcg of vitamin B12 |
| About 10 mg to about 2000 mg of krill oil; and/or | About 10 mg to about 1000 mg of oleic acid; and/or |
| About 10 mg to about 2000 mg of red palm oil | About 1 mg to about 1000 mg of linoleic acid; and/or |
| | About 1 mg to about 1000 mg of tocotrienols; and/or |
| | About 1 mg to about 1000 mg of tocopherols; and/or |
| | About 1 mg to about 1000 mg beta-carotene; and/or |
| | About 1 mg to about 1000 mg alpha-carotene; and/or |

TABLE 1-continued

| First compartment | Second compartment |
|---|---|
| | About 0.1 mg to about 1000 mg of squalene; and/or
Abou 1 mg to about 1000 mg of a plant sterol; and/or
Abou 0.01 mg to about 1000 mg of CoQ10; and/or
About 1 mg to about 5000 mg of a multivitamin |
| About 10 mg to about 2000 mg of krill oil; and/or
About 10 mg to about 2000 mg of an omega-3 oil, such as, for example, docosahexaenoic acid (DHA) | About 1 mg to about 1000 mg of vitamin C; and/or
About 1 mg to about 1000 mg of zinc; and/or
About 1 mg to about 1000 mg of dicalcium phosphate; and/or
About 10 IU to about 3000 IU of vitamin D; and/or
About 10 mcg to about 1000 mcg of vitamin K; and/or
About 0.1 mg to about 1000 mg of magnesium; and/or
About 1 mg to about 1000 mg of calcium |
| About 10 mg to about 2000 mg of krill oil | About 1 mg to about 5000 mg of a multivitamin; and/or
About 0.01 mg to about 1000 mg of CoQ10; and/or
About 10 IU to about 4000 IU of vitamin A; and/or
About 10 IU to about 3000 IU of vitamin D or vitamin D3; and/or
About 10 IU to about 3000 IU of vitamin E; and/or
About 10 mcg to about 1000 mcg of biotin; and/or
About 0.1 mcg to about 1000 mcg of folic acid; and/or
About 1 mg to about 1000 mg of niacin; and/or
About 1 mg to about 1000 mg of panthothenic acid; and/or
About 1 mg to about 1000 mg of vitamin B1; and/or
About 1 mg to about 1000 mg of vitamin B2; and/or
About 1 mg to about 1000 mg of vitamin B6; and/or
About 10 mcg to about 1000 mcg of vitamin B12; and/or
About 1 mg to about 1000 mg of vitamin C; and/or
About 10 mcg to about 1000 mcg of vitamin K; and/or
About 1 mg to about 1000 mg of calcium; and/or
About 1 mcg to about 1000 mcg of chromium; and/or
About 0.1 mg to about 100 mg of copper; and/or
About 0.01 mg to about 100 mg of iodine; and/or
About 0.1 mg to about 1000 mg of magnesium; and/or
About 0.1 mg to about 1000 mg of magnesium stearate; and/or
About 0.1 mg to about 100 mg of manganese; and/or
About 1 mcg to about 1000 mcg of molybdenum; and/or
About 1 mg to about 100 mg of phosphorous; and/or
About 1 mcg to about 200 mcg of selenium; and/or
About 1 mg to about 1000 mg of zinc |
| About 10 mg to about 2000 mg of red palm oil | About 10 mg to about 1000 mg of ginseng; and/or
About 0.01 mg to about 1000 mg of CoQ10; and/or |

TABLE 1-continued

| First compartment | Second compartment |
|---|---|
| About 10 mg to about 2000 mg of krill oil | About 10 mcg to about 1000 mcg of vitamin B12; and/or<br>About 1 mg to about 1000 mg of caffeine<br>About 10 IU to about 3000 IU of vitamin D or vitamin D3; and/or<br>About 1 mg to about 1000 mg of calcium |
| About 10 mg to about 2000 mg of an omega-3 oil | About 1 million to about 100 billion CFUs of a probiotic |
| About 10 mg to about 2000 mg of krill oil | About 0.01 mg to about 100 mg of vitamin K2; and/or<br>About 10 mg to about 1000 mg of glucosamine; and/or<br>About 1 mg to about 1000 mg of UC2 collagen |
| About 10 mg to about 2000 mg of an omega-3 oil, such as, for example, alpha - linolenic acid (ALA) | About 1 mg to about 1000 mg of caffeine or caffeine beadlets |
| About 10 mg to about 2000 mg of ginger oil | About 10 mg to about 1000 mg of curcumin |
| About 10 mg to about 2000 mg of an omega-3 oil | About 10 IU to about 3000 IU of vitamin D or vitamin D3; and/or<br>About 1 IU to about 3000 IU of vitamin E; and/or<br>About 0.1 mcg to about 1000 mcg of folic acid; and/or<br>About 1 mg to about 1000 mg of vitamin B2; and/or<br>About 1 mg to about 1000 mg of vitamin B6; and/or<br>About 1 mcg to about 1000 mcg of vitamin B12; and/or<br>About 1 mg to about 1000 mg of vitamin C; and/or<br>About 1 mg to about 1000 mg of iron; and/or<br>About 1 mg to about 1000 mg of dicalcium phosphate |
| About 10 mg to about 2000 mg of krill oil | About 10 IU to about 3000 IU of vitamin D or vitamin D3; and/or<br>About 0.01 mg to about 100 mg of vitamin K2; and/or<br>About 10 mg to about 1000 mg of vitamin E tocotrienols |
| About 10 mg to about 2000 mg of lavender oil | About 1 mg to about 1000 mg of melatonin; and/or<br>About 10 mg to about 1000 mg of passion flower; and/or<br>About 10 mg to about 1000 mg of lemon or lemon extract |
| About 10 mg to about 2000 mg of conjugated linoleic acid (CLA) | About 10 mg to about 1000 mg of a combination of piper betle leaf and/or dolichos biflorus seed extract, such as LOWAT |
| About 10 mg to about 2000 mg of krill oil | About 10 mg to about 500 mg of aspirin |

Table 2 below shows various dimensions of standard and elongated TORPAC capsule sizes, which may be used in some embodiments described herein.

TABLE 2

| CAPSULE SIZE | 000 | 00E | 00 | 00LQ | 0E | 0 | 1 | 2 | 3 | 4 |
|---|---|---|---|---|---|---|---|---|---|---|
| WEIGHT | | | | | | | | | | |
| Average Weight (mg) | 158 | 130 | 123 | 132 | 107 | 99 | 76 | 61 | 48 | 38 |
| tolerance | ±10 | ±10 | ±7 | ±4 | ±7 | ±6 | ±5 | ±4 | ±3 | ±3 |
| CAPACITY | | | | | | | | | | |
| Volume Capacity (ml) | 1.37 | 1.02 | 0.95 | 0.95 | 0.77 | 0.68 | 0.48 | 0.36 | 0.27 | 0.20 |

TABLE 2-continued

| CAPSULE SIZE | 000 | 00E | 00 | 00LQ | 0E | 0 | 1 | 2 | 3 | 4 |
|---|---|---|---|---|---|---|---|---|---|---|
| | Weight Capacity (mg) | | | | | | | | | |
| density of dosing powder | | | | | | | | | | |
| 0.6 g/ml | 822 | 612 | 570 | 570 | 462 | 408 | 288 | 216 | 162 | 120 |
| 0.8 g/ml | 1096 | 816 | 760 | 760 | 616 | 544 | 384 | 288 | 216 | 160 |
| 1.0 g/ml | 1370 | 1020 | 950 | 950 | 770 | 680 | 480 | 360 | 270 | 200 |
| 1.2 g/ml | 1644 | 1224 | 1140 | 1140 | 924 | 816 | 576 | 432 | 324 | 240 |
| OVERALL CLOSED LENGTH | | | | | | | | | | |
| (mm) | 26 | 25.4 | 23.4 | 23.4 | 23.4 | 21.6 | 19.4 | 17.6 | 15.7 | 14.3 |
| tolerance | ±0.3 | ±0.3 | ±0.3 | ±0.3 | ±0.3 | ±0.3 | ±0.3 | ±0.3 | ±0.3 | ±0.3 |
| (inches) | 1.024 | 1 | 0.921 | 0.921 | 0.921 | 0.85 | 0.764 | 0.693 | 0.618 | 0.563 |
| tolerance | ±0.012 | ±0.012 | ±0.012 | ±0.012 | ±0.012 | ±0.012 | ±0.012 | ±0.012 | ±0.012 | ±0.012 |
| INDIVIDUAL LENGTHS (CAP & BODY) | | | | | | | | | | |
| CAP (mm) | 12.9 | 12.94 | 11.8 | 11.8 | 11.9 | 10.85 | 9.85 | 8.8 | 8 | 7.2 |
| tolerance | ±0.35 | ±0.35 | ±0.35 | ±0.35 | ±0.35 | ±0.35 | ±0.35 | ±0.35 | ±0.35 | ±0.35 |
| BODY (mm) | 21.9 | 22.38 | 20.1 | 20.1 | 20 | 18.45 | 16.4 | 15.15 | 13.45 | 12.1 |
| tolerance | ±0.35 | ±0.35 | ±0.35 | ±0.35 | ±0.35 | ±0.35 | ±0.35 | ±0.35 | ±0.35 | ±0.35 |
| CAP (inches) | 0.508 | 0.509 | 0.464 | 0.464 | 0.468 | 0.427 | 0.388 | 0.346 | 0.315 | 0.283 |
| tolerance | ±0.014 | ±0.014 | ±0.014 | ±0.014 | ±0.014 | ±0.014 | ±0.014 | ±0.014 | ±0.014 | ±0.014 |
| BODY (inches) | 0.862 | 0.881 | 0.791 | 0.791 | 0.787 | 0.726 | 0.646 | 0.596 | 0.529 | 0.476 |
| tolerance | ±0.014 | ±0.014 | ±0.014 | ±0.014 | ±0.014 | ±0.014 | ±0.014 | ±0.014 | ±0.014 | ±0.014 |
| EXTERNAL DIAMETER | | | | | | | | | | |
| CAP (mm) | 9.94 | 8.58 | 8.56 | 8.56 | 7.66 | 7.65 | 6.96 | 6.39 | 5.85 | 5.33 |
| BODY (mm) | 9.55 | 8.25 | 8.23 | 8.23 | 7.35 | 7.35 | 6.63 | 6.12 | 5.60 | 5.08 |
| CAP (inches) | 0.391 | 0.338 | 0.337 | 0.337 | 0.302 | 0.301 | 0.274 | 0.252 | 0.23 | 0.21 |
| BODY (inches) | 0.376 | 0.325 | 0.324 | 0.324 | 0.289 | 0.289 | 0.261 | 0.241 | 0.22 | 0.2 |

Recommended Storage Conditions: 59°-77° F./15°-25° C. RH 35-65%

Table 3 below shows additional dimensions of standard and elongated TORPAC capsule sizes, which may be used in some embodiments described herein.

TABLE 3

| Size | Typical Fill Weights (mg) Actual Fill Weights may vary and depend on powder characteristics Powder Density | | | Volume Theoretical (ml) | Locked Length +/−0.76 (mm) | Tolerance Component | External Diam. (mm) | Cut Length +/−0.51 (mm) | Single Wall Thickness +/−0.03 (mm) | Weight (Avg. of 100) +/−10% (mg) |
|---|---|---|---|---|---|---|---|---|---|---|
| | 0.45 (Light) | 0.70 (Typical) | 1.00 (Heavy) | | | | | | | |
| 000 | 615 | 960 | 1370 | 1.37 | 26.14 | Cap | 9.91 | 12.95 | 0.112 | 163 |
| | | | | | | Body | 9.55 | 22.20 | 0.110 | |
| 00 | 430 | 665 | 950 | 0.95 | 23.30 | Cap | 8.53 | 11.74 | 0.109 | 118 |
| | | | | | | Body | 8.18 | 20.22 | 0.107 | |
| 0 | 305 | 475 | 680 | 0.68 | 21.70 | Cap | 7.65 | 10.72 | 0.107 | 96 |
| | | | | | | Body | 7.34 | 18.44 | 0.104 | |
| 1 | 225 | 350 | 500 | 0.50 | 19.40 | Cap | 6.91 | 9.78 | 0.104 | 76 |
| | | | | | | Body | 6.63 | 16.61 | 0.102 | |
| 2 | 165 | 260 | 370 | 0.37 | 18.00 | Cap | 6.35 | 8.94 | 0.102 | 61 |
| | | | | | | Body | 6.07 | 15.27 | 0.099 | |
| 3 | 135 | 210 | 300 | 0.30 | 15.90 | Cap | 5.82 | 8.08 | 0.092 | 48 |
| | | | | | | Body | 5.56 | 13.59 | 0.890 | |
| 4 | 95 | 145 | 210 | 0.21 | 14.30 | Cap | 5.31 | 7.21 | 0.096 | 38 |
| | | | | | | Body | 5.05 | 12.19 | 0.091 | |
| 5 | 60 | 90 | 130 | 0.13 | 11.10 | Cap | 4.91 | 6.20 | 0.089 | 28 |
| | | | | | | Body | 4.68 | 9.32 | 0.086 | |

Although the present invention has been described in considerable detail with reference to certain preferred embodiments thereof, other versions are possible. Therefore, the spirit and scope of the appended claims should not be limited to the description and the preferred versions contained within this specification. Modifications and improvements to the disclosed embodiments will be apparent to those skilled in the art in light of this disclosure, and are intended to fall within the scope of the pending claims.

The invention claimed is:

1. A multi-compartment capsule comprising:
   a body;
   a diaphragm, having two sidewalls and a bottom, extending into the body and defining a first compartment between an outer surface of the diaphragm and an inner surface of the body, the first compartment holding an oil; and a cap mounted to an outer surface of the body and opposed to the diaphragm, and defining a second compartment between an inner surface of the diaphragm and the cap, the second compartment holding an oil-soluble ingredient;

wherein the two sidewalls of the diaphragm extend along the inner surface of the body and are aligned with an open end of the body; and wherein the first compartment and the second compartment are configured to simultaneously release the oil and the oil-soluble ingredient during digestion of the multi-compartment capsule.

2. The capsule of claim 1, wherein the first compartment is hermetically sealed.

3. The capsule of claim 1, wherein the oil is selected from the group consisting of omega-3 oil, red palm oil, fish oil, hill oil, walnut oil, saw palmetto oil, castor oil, garlic oil, flaxseed oil, canola oil, soybean oil, *Cannabis* oil, argan oil, coconut oil, peppermint oil, evening primrose oil, oregano oil, emu oil, cod liver oil, algae oil, grape seed oil, rose oil, clove oil, vitamin E oil, blueberry seed oil, raspberry seed oil, pumpkin seed oil, hemp oil, alpha-linolenic acid, conjugated linoleic acid, docosahexaenoic acid, ginger oil, lavender oil, and combinations thereof.

4. The capsule of claim 3, wherein the omega-3 oil is selected from the group consisting of alpha-linolenic acid, docosahexaenoic acid, eicosapentaenoic acid, hill oil, fish oil, walnut oil, flaxseed oil, canola oil, soybean oil, algae oil, and combinations thereof.

5. The capsule of claim 1, wherein the oil-soluble ingredient is a powder, a granule, a semi-solid, a beadlet, a microbead, or a combination thereof.

6. The capsule of claim 1, wherein the bottom of the diaphragm has a shape selected from the group consisting of curved and flattened.

7. The capsule of claim 1, wherein the oil comprises an omega-3 oil and the oil-soluble ingredient is selected from the group consisting of a multivitamin powder, coenzyme Q 10, a statin, and combinations thereof.

8. The capsule of claim 1, wherein the oil comprises an omega-3 oil and the oil-soluble ingredient is vitamin K2.

9. The capsule of claim 1, wherein the oil comprises alpha-linolenic acid and the oil-soluble ingredient is coenzyme Q 10.

10. The capsule of claim 1, wherein the oil is red palm oil, and the oil-soluble ingredient is selected from the group consisting of vitamin D, vitamin K2, a multivitamin, and combinations thereof.

11. A multi-compartment capsule comprising:

a body;

a diaphragm, having two sidewalls and a bottom, extending into the body and defining a first compartment between an outer surface of the diaphragm and an inner surface of the body, the first compartment holding an oil-soluble ingredient; and a cap mounted to an outer surface of the body and opposed to the diaphragm, and defining a second compartment between an inner surface of the diaphragm and the cap, the second compartment holding an oil;

wherein the two sidewalls of the diaphragm extend along the inner surface of the body and are aligned with an open end of the body; and wherein the first compartment and the second compartment are configured to simultaneously release the oil and the oil-soluble ingredient during digestion of the multi-compartment capsule.

12. The capsule of claim 11, wherein the second compartment is sealed to prevent oil leakage.

13. The capsule of claim 11, wherein the oil is selected from the group consisting of omega-3 oil, red palm oil, fish oil, hill oil, walnut oil, saw palmetto oil, castor oil, garlic oil, flaxseed oil, canola oil, soybean oil, *Cannabis* oil, argan oil, coconut oil, peppermint oil, evening primrose oil, oregano oil, emu oil, cod liver oil, algae oil, grape seed oil, rose oil, clove oil, vitamin E oil, blueberry seed oil, raspberry seed oil, pumpkin seed oil, hemp oil, alpha-linolenic acid, conjugated linoleic acid, docosahexaenoic acid, ginger oil, lavender oil, and combinations thereof.

14. The capsule of claim 11, wherein the oil-soluble ingredient is selected from the group consisting of an oil, a liquid, a powder, a granule, a gel, a semi-solid, a beadlet, a microbead, and combinations thereof.

15. The capsule of claim 11, wherein the bottom of the diaphragm has a shape selected from the group consisting of curved and flattened.

16. A multi-compartment capsule comprising:

a body;

a diaphragm, having two sidewalls and a bottom, extending into the body and defining a first compartment between an outer surface of the diaphragm and an inner surface of the body, the first compartment holding an oil; and a cap mounted to an outer surface of the body and opposed to the diaphragm, and defining a second compartment between an inner surface of the diaphragm and the cap, the second compartment holding an oil-suspendable ingredient that has increased bioavailability after suspension in the oil;

wherein the two sidewalls of the diaphragm extend along the inner surface of the body and are aligned with an open end of the body; and wherein the first compartment and the second compartment are configured to simultaneously release the oil and the oil-suspendable ingredient during digestion of the multi-compartment capsule.

17. A multi-compartment capsule comprising:

a body;

a diaphragm, having two sidewalls and a bottom, extending into the body and defining a first compartment between an outer surface of the diaphragm and an inner surface of the body, the first compartment holding an omega-3 oil comprising an eicosapentaenoic acid; and a cap mounted to an outer surface of the body and opposed to the diaphragm, and defining a second compartment between an inner surface of the diaphragm and the cap, the second compartment holding a statin;

wherein the two sidewalls of the diaphragm extend along the inner surface of the body and are aligned with an open end of the body; and wherein the first compartment and the second compartment are configured to simultaneously release the omega-3 oil and the statin during digestion of the multi-compartment capsule.

18. A multi-compartment capsule comprising:

a body;

a diaphragm, having two sidewalls and a bottom, extending into the body and defining a first compartment between an outer surface of the diaphragm and an inner surface of the body, the first compartment holding a statin; and a cap mounted to an outer surface of the body and opposed to the diaphragm, and defining a second compartment between an inner surface of the diaphragm and the cap, the second compartment holding an omega-3 oil comprising an eicosapentaenoic acid;

wherein the two sidewalls of the diaphragm extend along the inner surface of the body and are aligned with an open end of the body; and wherein the first compartment and the second compartment are configured to simultaneously release the omega-3 oil and the statin during digestion of the multi-compartment capsule.

\* \* \* \* \*